United States Patent
Hammon et al.

(10) Patent No.: US 7,319,166 B2
(45) Date of Patent: Jan. 15, 2008

(54) METHOD OF PURIFYING A RAW MELT OF AT LEAST ONE MONOMER BY CRYSTALLIZATION

(75) Inventors: Ulrich Hammon, Mannheim (DE); Bernd Eck, Viernheim (DE); Dieter Baumann, Walldorf (DE); Joerg Heilek, Bammental (DE); Klaus Joachim Mueller-Engel, Stutensee Blankenloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 752 days.

(21) Appl. No.: 10/476,187

(22) PCT Filed: May 2, 2002

(86) PCT No.: PCT/EP02/04783

§ 371 (c)(1),
(2), (4) Date: Nov. 6, 2003

(87) PCT Pub. No.: WO02/090310

PCT Pub. Date: Nov. 14, 2002

(65) Prior Publication Data

US 2004/0133015 A1   Jul. 8, 2004

(30) Foreign Application Priority Data

May 10, 2001   (DE) ............................... 101 22 788

(51) Int. Cl.
*C07C 51/43*   (2006.01)
*C07D 207/00*  (2006.01)

(52) U.S. Cl. ...................... 562/600; 548/543

(58) Field of Classification Search ................ 562/600; 548/543
See application file for complete search history.

(56) References Cited

U.S. PATENT DOCUMENTS

| | | | |
|---|---|---|---|
| 4,776,177 A | | 10/1988 | Jancic et al. |
| 5,329,021 A | * | 7/1994 | Cohen et al. ............... 548/543 |
| 5,504,247 A | | 4/1996 | Saxer et al. |
| 5,855,743 A | | 1/1999 | Herbst et al. |
| 6,458,956 B1 | | 10/2002 | Sutoris et al. |

FOREIGN PATENT DOCUMENTS

| | | | |
|---|---|---|---|
| DE | 26 06 364 | | 9/1977 |
| DE | 100 39 025 A1 | * | 8/2000 |
| DE | 199 26 082 | | 12/2000 |
| DE | 199 38 841 | | 2/2001 |
| DE | 100 03 497 | | 4/2001 |
| DE | 100 03 498 | | 8/2001 |
| DE | 100 26 407 | | 12/2001 |
| DE | 100 39 025 | | 2/2002 |
| EP | 0 216 545 | | 10/1990 |
| EP | 0 616 998 | | 9/1994 |
| EP | 0 722 926 | | 7/1996 |
| WO | 94/18166 | | 8/1994 |
| WO | 00/45928 | | 8/2000 |

* cited by examiner

*Primary Examiner*—Kamal A. Saeed
*Assistant Examiner*—Janet L. Coppins
(74) *Attorney, Agent, or Firm*—Oblon, Spivak, McClelland, Maier & Neustadt, P.C.

(57) ABSTRACT

The invention relates to a method for purifying a raw melt of at least one monomer by crystallization, wherein suspension crystallization is initially used and the resulting remaining melt or the suspension crystals that have been molten once again and separated are subjected to a mechanical separation operation before undergoing subsequent purification by crystallization.

9 Claims, 1 Drawing Sheet

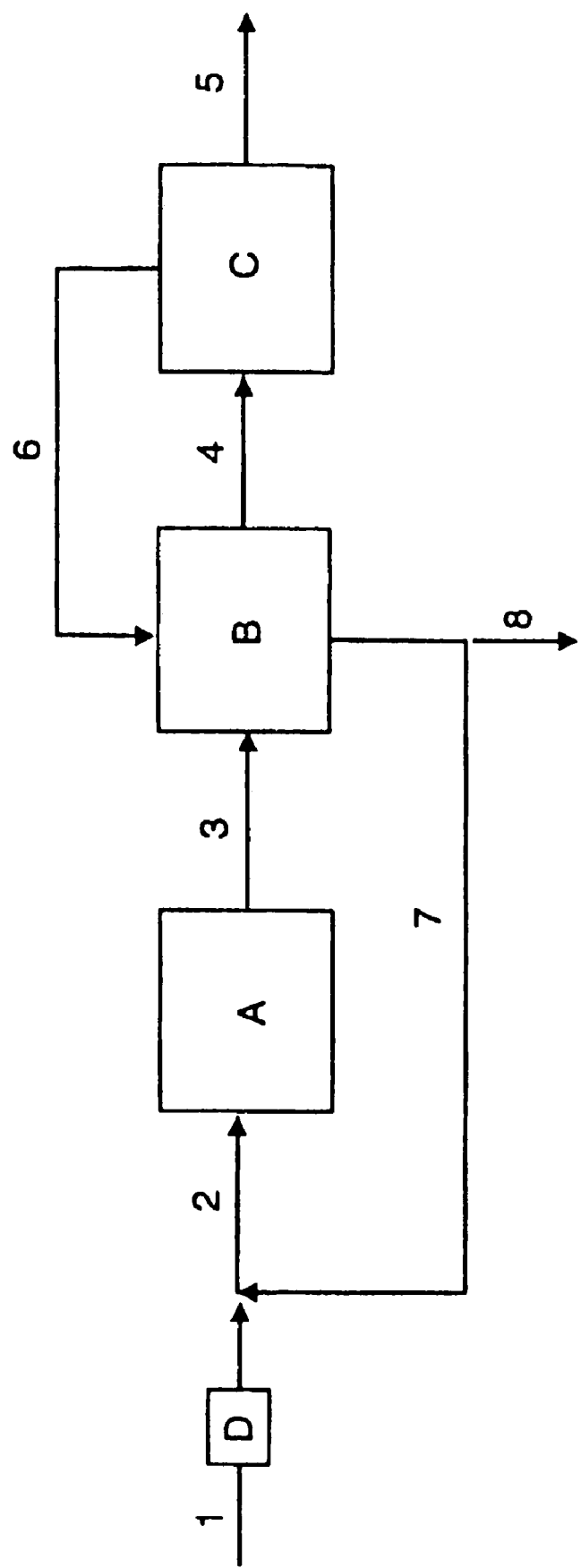

METHOD OF PURIFYING A RAW MELT OF AT LEAST ONE MONOMER BY CRYSTALLIZATION

BACKGROUND OF THE INVENTION

1. Field of the Invention

The present invention relates to a process for the purification of a crude melt of at least one monomer by crystallization, in which the crude melt to be purified is subjected to a suspension crystallization, the monomer crystals produced during the suspension crystallization and suspended in residual melt are separated from the residual melt by using a first mechanical separation operation and, in at least one further crystallization stage, the residual melt remaining after the first mechanical separation operation and/or the monomer crystals which have been separated off and if necessary washed are further purified by crystallization after they have been melted.

2. Discussion of the Background

The term monomer in this document is intended to include chemical compounds which have at least one ethylenically unsaturated double bond.

Owing to the one or more ethylenically unsaturated double bonds, monomers form extremely reactive compounds which are used, inter alia, for the preparation of polymers. Typical examples of monomers are N-vinylpyrrolidone, acrylic acid, methacrylic acid and the alkyl esters of the abovementioned acids.

Usually, monomers are produced by chemical synthesis from suitable raw materials. Particularly because of impurities already present in the raw materials and owing to undesired secondary reactions, they are usually not present directly in pure form but are obtained as a component of mixtures from which they have to be isolated. Historically, in particular separation operations involving rectification or extraction and rectification are used as separation processes in this context (cf. for example EP-A 722926).

The disadvantage of these separation processes is that they have a high energy consumption since high reflux ratios and/or rectification columns having a large number of theoretical plates have to be employed.

As an alternative, the melt crystallization procedure for the preparation of pure monomers has been attracting increasing interest very recently (cf. for example EP-A 616998).

A crude melt of at least one monomer is obtained as a result of the synthesis and, if required, initial thermal and/or extraction separation stages. In this document, this is understood as meaning liquids which contain the one or more monomers and on cooling deposit as a first solid crystals of the one or more monomers which contain less of substances differing from the one or more monomers than does the crude melt itself.

This means that the term crude melt used here is not applicable when, for example, extracting agent or another component separates out as a first solid on cooling instead of the one or more monomers.

As a rule, the crude melts which are important according to the invention and comprise the one or more monomers contain small amounts of added polymerization inhibitors present in solution (cf. for example DE-A 19938841), which are intended to suppress an undesired free radical polymerization of the one or more monomers under the action of heat and/or light.

The one or more monomers can then be separated by crystallization from the above-defined crude melts of the one or more monomers in a manner known per se by the action of low temperatures, and a purified melt (in solid or in liquid form) of the one or more monomers can thus be prepared (cf. for example DE-A 19926082, WO 00/45928, WO 94/18166, DE-A 10026407, DE-A 10039025, DE-A 10003498 and DE-A 10003497).

Very generally, the contaminated crude melt is partially solidified by cooling. Depending on the phase equilibrium, the monomer crystals formed have a lower impurity content than the liquid residual melt remaining behind. The purely thermodynamically determined separation effect described above is reduced by the inclusion of liquid during the crystallization process and by the residual melts still adhering to the solid after a solid/liquid separation.

For achieving high purities and/or yields, a plurality of successive crystallization steps (also referred to as crystallization stages here) are often therefore required, i.e. the crystals obtained in a first crystallization stage, if necessary after they have been washed with a suitable solvent or with a melt of already purified crystals for removing residual melt, are remelted and are subjected to a further crystallization step, etc.

In order to render the yield economical, the residual melt obtained in the first crsytallization step is as a rule also subjected to at least one further crystallization step (in a further crystallization stage).

In general, different melt crystallization processes may be used for the purification of crude melts of at least one monomer by crystallization. In the layer crystallization processes, the one or more monomers are frozen out in the form of cohesive, firmly adhering layers.

The solid/liquid separation is effected by simply allowing the residual melt to flow away. The purified crystals can then be melted or can be dissolved in a desired solvent for further use.

In principle, a distinction is made between static and dynamic layer crystallization processes.

In the static process, the crude melt to be purified is introduced, for example, into tube-bundle heat exchangers or modified plate heat exchangers and then partially solidified by slow temperature reduction on the secondary side. After freezing, the residual melt is discharged and the crystal layer separated off is then melted as purified melt (pure melt), if necessary in stages. The heat and mass transfer to the separation or crystal layer surfaces is effected only by free convection.

Forced convection of the crude melt is typical of the dynamic layer crystallization of crude melts. This can be effected by pumping the crude melt through tubes with plug flow (e.g. German Laid-Open Application DOS 2,606,364), by feeding the crude melt as a falling film (e.g. EP-A 616998) or by passing inert gas into a tube filled with melt or by pulsation.

In the suspension crystallization process, a crystal suspension which contains the crystals separated off suspended in the residual melt is produced from the crude melt by the action of low temperatures. The solid crystals may be growing directly in suspension or may be deposited as a layer on a cooled wall, from which they are subsequently scraped off and resuspended in the residual melt. The separation of the deposited crystals from the residual melt is effected in the case of a crystal suspension usually by a mechanical separation operation (for example pressing, filtration, centrifuging and/or in wash columns).

The use of a combination of different crystallization methods is now frequently recommended for efficient separation of at least one monomer from the crude melts (cf. for example EP-A 616998).

For example, the crude melt can first be subjected to a suspension crystallization. The crystals which separate out thereby and are suspended in the residual melt are then separated from the residual melt by a mechanical separation operation and either are themselves the desired pure end product or are remelted, if necessary after they have been washed with, for example pure product melt (for example by resuspension therein) and are further purified in a further crystallization stage. This further crystallization stage may once again be a suspension crystallization but it may also be a layer crystallization. In a corresponding manner, the remaining residual melt can be further purified in a further crystallization stage. Although this can in principle likewise once again be a suspension crystallization, it may also be a layer crystallization.

Typical of all crystallization processes is that they have constrictions, i.e. regions with a narrow flow cross section. Thus, falling-film crystallizers usually contain, for example, internals which leave only a small flow cross section. The melt to be purified passes through this constriction only in the form of a thin film. Behind the constriction, this film is maintained and flows as a falling film down a cooled wall on which crystals are deposited during the flow process (cf. for example EP-B 218545).

In another manner, the separation of a crystal suspension into crystals and residual melt is effected almost always via cross sections through which only residual melt but not the suspended crystals can pass (for example via a two- or three-dimensional network of such cross sections in the case of filtration or in a screen centrifuge).

Usually, the crystallization processes for the purification of a crude melt of at least one monomer are carried out more or less continuously (or semicontinuously). A precondition for high space-time yields is that the narrow flow cross sections described are not blocked.

In contrast to the fractional layer crystallization process used in WO 0045928, there should be no problem with solid imported from the preceding suspension crystallization stage in the downstream crystallization stages (which are used for the further purification of the suspension crystals or for the further purification of the residual melt) in the process described in the preamble, in which it is essential initially to use a suspension crystallization stage. With the mechanical isolation of the suspension crystals, it is also intended to separate off other solids precipitated on reduction of the temperature, so that the remaining residual melt should be free from foreign solids.

However, the remelted suspension crystals should also be free from solids, and any concomitantly deposited foreign solids would in fact also go into solution again on melting.

When the process described in the preamble and intended for the purification of a crude melt of at least one monomer by crystallization was carried out in practice, such undesirable blockages occurred again and again (in particular in the case of acrylic acid, methacrylic acid and N-vinylpyrrolidone) in the crystallization stages for the further purification of a residual melt or of the suspension crystals, which crystallization stages follow the suspension crystallization stage to be used at the outset. This is particularly the case when the characteristic length of the constrictions is $\leq 5$ mm. It is noteworthy that the material causing the blockage do not consist of crystals since the blockage generally could not be eliminated by heating above the melting point of the crystals.

SUMMARY OF THE INVENTION

It is an object of the present invention to improve the process for the purification of a crude melt of at least one monomer by crystallization, which process is described in the preamble.

We have found that this object is achieved by a process for the purification of a crude melt of at least one monomer by crystallization, in which the crude melt to be purified is subjected to a suspension crystallization, the monomer crystals produced during the suspension crystallization and suspended in residual melt are separated from the residual melt by using a first mechanical separation operation and, in at least one further crystallization stage, the residual melt remaining after the first mechanical separation operation and/or the monomer crystals which have been separated off and if necessary washed are further purified after they have been melted, wherein the residual melt and/or the remelted monomer crystals are subjected to at least one further mechanical solid/liquid separation operation on their way into the one or more further crystallization stages.

BRIEF DESCRIPTION OF DRAWINGS

The FIGURE shows a flow chart of the process according to the invention.

DETAILED DESCRIPTION OF THE INVENTION

The background of the claimed invention is the surprising finding that, for example, the residual melts which are separated off in the novel process after the suspension crystallization to be used at the outset are not actually free of problems with solids but, in spite of the use of polymerization inhibitors, contain very small amounts of polymer of the one or more monomers to be purified, which polymer is present in disperse (partly colloidal) distribution, undesirable and virtually invisible and causes a blockage when the purification process is carried out more or less continuously or semicontinuously over a prolonged period.

Particularly critical is the described situation where the polymers-frequently do not have a particularly high molecular weight and are therefore often tacky.

The novel process is particularly suitable when the melting point of the relevent monomer is $\leq 200°$ C., preferably $\leq 150°$ C., particularly preferably $\leq 100°$ C. or from 5 to 20° C.

It is particularly suitable for the preparation of purified melts of acrylic acid, methacrylic acid, alkyl esters of the abovementioned acids and N-vinylpyrrolidone.

In principle, all separation operations which are suitable for separating solids from liquids are suitable as a first mechanical separation operation to be used according to the invention. These are, for example, separation operations involving filtration, settling and centrifuging. Processes involving centrifuging (e.g. screen centrifuges) and/or wash columns (cf. DE-A 10017903) are preferably used.

In principle, all separation operations which are suitable for separating solids (in particular for finely divided ones) from liquids are likewise suitable as at least one further mechanical solid/liquid separation operation to be used according to the invention. Separation operations involving filtration and centrifuging are particularly suitable. Filter materials which may be used are bar sieves, perforated sieves, woven fabric screens, filter nonwovens, fiber layers, woven fiber fabrics, sintered material or beds (for example including sand). The pore size of the filter material used above is expediently from 50 to 1 000 μm with one or more further mechanical solid/liquid separation operations to be used according to the invention. Frequently, it should be from 100 to 500 μm. Often, however, a range of from 10 to 20 μm or less is also to be used. The filtration can be effected as a pressure or vacuum filtration. Of course, it may also be carried out by centrifuging using a screen centrifuge. Settling apparatuses (decanters, hydrocyclones, lamellar clarifiers, dwell tanks) are less preferred for the one or more further mechanical separation operations for the novel process. According to the invention, the filter may also be mounted directly in the inlet to the one or more further crystallization stages.

The novel process is suitable in particular when the crude melt is subjected to suspension crystallization and the resulting crystal suspension is separated into residual melt and crystals, as described in DE-A 10039025, with the aid of a wash column.

This is true in particular when the relevant monomer is acrylic acid and has been prepared by the route of heterogeneously catalyzed gas-phase oxidation, as described in DE-A 19909923. According to the invention, it is advantageous if the residual melt remaining after the use of the first mechanical separation operation is heated at least to the melting point of the pure crystals before it is fed to the next crystallization stage.

Examples and comparative example (the reference numbers used in the 340 kg/h of a crude acrylic acid (crude melt) having the following content were produced analogously to example 2 of DE-A 19909923 by fractional condensation of a cooled product gas mixture of a two-stage heterogeneously catalyzed gas-phase oxidation of propene:

| | |
|---|---|
| Acrylic acid | 97.3% by weight, |
| acetic acid | 0.8% by weight, |
| propionic acid | 500 ppm by weight, |
| furfural | 700 ppm by weight, |
| maleic anhydride | 40 ppm by weight, |
| benzaldehyde | 200 ppm by weight, |
| water | 1.3% by weight and |
| phenothiazine (polymerization inhibitor) | 150 ppm by weight |

Said crude acrylic acid (1) was passed via a wire basket filter D and fed to a suspension crystallizer A. Standard chemical pumps of the type CPK (i.e. centrifugal pumps having a double axial face seal), as produced, for example, by KSB or Allweiler, were used for this purpose. The suspension crystallizer was a cooling-disk crystallizer (7 cooling disks, total cooling area about 16 m², the diameter of the circular cooling disks was 1.25 m, 2 500 l internal volume). The feed temperature of the crude acrylic acid was 25° C. The heat of crystallization was removed via the cooling surfaces. The residual melt was cooled to 7° C. during passage through the cooling-disk crystallizer. The crystal suspension, which had a solids content of about 25% of the mixture, was fed continuously from the suspension crystallizer to a two-stage reciprocating-conveyor centrifuge B (reciprocating-conveyor centrifuges are described, for example, in the brochure WB 210/11.92AL from Siebtechnik, Mülheim an der Ruhr, Germany; in a 2-stage reciprocating-conveyor centrifuge, a rotating (larger) outer screen drum (representing the second stage) and a (smaller) rotating inner screen drum (representing the first stage) are arranged concentrically; the outer screen drum executes only rotational movements but no translational movement; the inner screen drum revolves at the same speed as the outer screen drum and is additionally moved back and forth in the axial direction by a hydraulic reciprocating piston; both drums have a screen structure for discharging the liquid; in the feed zone of the inner screen drum, the major part of the residual melt is immediately forced through the screen orifices by centrifugal force; the solid remains behind as a filter cake on the screen; during the axial return movement of the inner drum, an amount of solid corresponding to the translational length is ejected at the free drum end into the outer screen drum and is further dewatered there; during the axial forward movement of the inner screen drum, the filter cake is pushed further stepwise into the outer screen drum (which as a rule is longer than the inner screen drum) and is finally ejected into a collecting channel) on which the suspension crystals were separated from the residual melt and additionally washed with a stream (6) (wash liquid comprised 23 kg/h of molten, washed crystals at 25° C.). The internal diameter of the first stage was 200 mm. The screen gap width of the first stage was 250 μm. The second stage was conical (the internal diameter widened from 250 mm to 310 mm and the screen gap width was 300 μm). The speed was 2 200 revolutions per minute. The number of strokes of the inner screen drum was 70 per minute.

The ejected washed crystals (4) were melted in a container C, and 227 kg/h of purified acrylic acid (5) having an acrylic acid content of >99% by weight were taken off. The residual melt separated off in stage B was partly (113 kg/h) discharged (8) but for the most part (660 kg/h) recycled (7), with the use of standard chemical pumps of the type CPK (i.e. centrifugal pumps having a double axial face seal), as produced, for example, by KSB or Allweiler, to the suspension crystallizer and combined with the stream (1) downstream of the wire basket filter D to give the transparent stream (2) which is optically free of solid and has a temperature of 15° C., in order to be fed to a further crystallization step.

After operation of the centrifuge B for about six weeks, overshooting of the crystal suspension occurred in the first stage, i.e. the liquid phase was no longer sufficiently separated off in the first stage and flowed in a channel-like manner, via the filter cake formed in the first stage, into the second stage. This is disadvantageous in that it results in an increase in the residual moisture of the crystals ejected from the second stage and irregular running of the centrifuge (due to the imbalance caused by the channel formation and filter cake deformation in the first stage), forcing a reduction in speed.

After the installation of two interchangeable filters (wire basket filters each having a screen area of 550 cm² and a screen size of 150 μm) in the recycle stream 7 to the suspension crystallizer, no overshooting of the suspension in the first stage was found under otherwise identical operating conditions, even after an operating time of more than four months.

Changing and cleaning of the interchangeable filters were carried out about once a week. Rubber-like, tacky polymer was present therein, which proved to be polyacrylic acid and could be washed out with aqueous sodium hydroxide solution and subsequently water.

We claim:

1. A process for the purification of a crude melt of at least one monomer by crystallization, in which the crude melt to be purified is subjected to a suspension crystallization, the monomer crystals produced during the suspension crystallization and suspended in residual melt are separated from the residual melt by using a first mechanical separation operation and, in at least one further crystallization stage, the residual melt remaining after the first mechanical separation operation and/or the monomer crystals which have been separated off and if necessary washed are further purified after they have been melted, wherein the residual melt and/or the remelted monomer crystals are subjected to at least one further mechanical solid/liquid separation operation on their way into the one or more further crystallization stages.

2. A process as claimed in claim 1, wherein the further purification of the residual melt by crystallization is effected by suspension crystallization.

3. A process as claimed in claim 1, wherein the further purification of the residual melt by crystallization is effected by falling-film crystallization.

4. A process as claimed in claim 1, wherein the one or more monomers are selected from the group consisting of acrylic acid, methacrylic acid and N-vinylpyrrolidone.

5. A process as claimed in claim 2, wherein the one or more monomers are selected from the group consisting of acrylic acid, methacrylic acid and N-vinylpyrrolidone.

6. A process as claimed in claim 3, wherein the one or more monomers are selected from the group consisting of acrylic acid, methacrylic acid and N-vinylpyrrolidone.

7. A process as claimed in claim 4, wherein the one or more monomers are selected from the group consisting of acrylic acid, methacrylic acid and N-vinylpyrrolidone.

8. A process for the purification of a crude melt of at least one monomer, comprising:
   subjecting the crude melt to a first suspension crystallization, thereby producing monomer crystals suspended in a residual melt,
   separating said monomer crystals from said residual melt by using a first mechanical separation operation, to obtain separated monomer crystals and a separated residual melt,
   subjecting the separated residual melt and/or remelted separated monomer crystals to at least one further mechanical solid/liquid separation operation on their way into one or more further crystallization stages;
   wherein said separated monomer crystals are optionally washed, and
   wherein said monomer has at least one ethylenically unsaturated double bond.

9. The process as claimed in claim 1, wherein said monomer has at least one ethylenically unsaturated double bond.

* * * * *